(12) United States Patent
Nimni et al.

(10) Patent No.: US 7,598,291 B2
(45) Date of Patent: Oct. 6, 2009

(54) METHODS AND COMPOSITIONS FOR ENHANCING COLLAGEN AND PROTEOGLYCAN SYNTHESIS IN THE SKIN

(76) Inventors: Marcel Nimni, 2800 Nielson Way #908, Santa Monica, CA (US) 90405; Bo Han, 8853 Longden Ave., Temple City, CA (US) 91780

( * ) Notice: Subject to any disclaimer, the term of this patent is extended or adjusted under 35 U.S.C. 154(b) by 553 days.

(21) Appl. No.: 10/933,114

(22) Filed: Sep. 2, 2004

(65) Prior Publication Data

US 2006/0045926 A1    Mar. 2, 2006

(51) Int. Cl.
  A61K 31/352    (2006.01)
  A61K 31/35     (2006.01)
(52) U.S. Cl. .................. 514/456; 514/453; 424/401
(58) Field of Classification Search .................. None
  See application file for complete search history.

(56) References Cited

U.S. PATENT DOCUMENTS

| | | | |
|---|---|---|---|
| 4,820,724 A | | 4/1989 | Nimni |
| 5,198,465 A | * | 3/1993 | Dioguardi .................. 514/474 |
| 5,487,776 A | | 1/1996 | Nimni |
| 5,709,868 A | | 1/1998 | Perricone |
| 5,804,168 A | * | 9/1998 | Murad .......................... 424/59 |
| 5,935,994 A | | 8/1999 | Nimni |
| 6,426,080 B1 | * | 7/2002 | Golz-Berner et al. ....... 424/401 |
| 6,565,912 B1 | | 5/2003 | Gugger et al. |
| 6,576,271 B2 | | 6/2003 | Nair et al. |

OTHER PUBLICATIONS

Entrez Protein Entry for human collagen, locus BAA04809, accessed Aug. 30, 2007.*
Podda, M. & Grundmann-Kollmann, M., "Low Molecular Weight Antioxidants and Their Role in Skin Aging," Clin. Exp. Dermatol. 26: 578-582 (2001).
Biewenga, G.P., et al., "The Pharmacology of the Antioxidant Lipoic Acid," Gen. Pharmacol. 29: 315-331 (1997).
Packer, L., "Antioxidant Properties of Lipoic Acid and Its Therapeutic Effects in Prevention of Diabetes Complications and Cataracts," Ann. N.Y. Acad. Sci. 738: 257-264 (1994).
Teichert, J. et al., "Investigations on the Pharmacokinetics of Alpha-Lipoic Acid in Healthy Volunteers," Int. J. Clin. Pharmacol. Ther.: 36: 625-268 (1998).
Hagen, T.M., et al., "(R)-Alpha-Lipoic Acid-Supplemented Old Rats Have Improed Mitochndrial Function, Decreased Oxidative Damage, and Increased.." FASEB J. 13: 411-418 (1999).
Lykkesfeldt, J. et al., "Age-Associated Decline in Ascorbic Acid Concentration, Recycling, and Biosynthesis in Rat Hepatocytes—Reversal with (R)-Alpha-Lipoic Acid Supp," FASE B Journal 12, 1183-1189 (1998).
Khanna, S. et al., "Cytokine-Induced Glucose Uptake in Skeletal Muscle: Redox Regulation and the Role of Alpha-Lipoic Acid," Am. J. Physiol. 276:R1327-R21333 (1999).
Podda, M. et al., "Kinetic Study of Cutaneous and Subcutaneous Distribution Following Topical Application of . . . ," Biochem. Pharmacol. 52: 627-633 (1996).
Cordoba, F. & Ninni, M., "Chondroitin Sulfate and Other Sulfate Containing Chondroprotective Agents May Exhibit Their Effect . . . " Osteoarthritis & Cartilage 11: 228-230 (2003).
Han, B., et al., "Proanthocyanidin: A Natural Crosslinking Reagent for Stailizing Collagen Matrices," J. Biomed. Mater. Res. 65A:118-24 (2003.

* cited by examiner

*Primary Examiner*—Michael G Hartley
*Assistant Examiner*—Nissa M Westerberg
(74) *Attorney, Agent, or Firm*—Michael B. Farber (57) ABSTRACT

A composition for application to the skin can stimulate the in vivo synthesis of collagen and proteoglycans and improve the appearance of the skin, increasing its elasticity and fullness. In general, a composition according to the present invention comprises: (1) an antioxidant compound in a quantity sufficient to enhance collagen synthesis in the skin; (2) an organic penetrant in which the antioxidant compound is soluble in a sufficient quantity that a concentration of the antioxidant compound sufficient to enhance collagen synthesis can be applied topically and penetrate the skin; (3) a mixture of essential amino acids; (4) a supplemental source of sulfur; and (5) a topical pharmaceutically acceptable carrier. The antioxidant compound can be lipoic acid, a lipoic acid analogue or derivative, a bioflavonoid, a constituent of ginkgo, or an isoflavone. The organic penetrant is preferably benzyl alcohol. Other ingredients, such as esters of tocopherol and ascorbic acid, can be included.

5 Claims, 10 Drawing Sheets

BABY GIRL
3 YEARS OLD, UNTREATED

FIGURE 7

35 YEAR OLD FEMALE
UNTREATED

FIGURE 8

18 YEAR OLD FEMALE
UNTREATED

Figure 9

SAME AS ABOVE
TREATED FOR 1 DAY

FIGURE 10

FEMALE. 61 YEARS OLD
UNTREATED

FIGURE 11

SAME AS ABOVE.
TREATED FOR 1 DAY

FIGURE 12

SAME
TREATED FOR 3 DAYS

Figure 13

SAME
TREATED FOR 6 DAYS

Figure 14

METHODS AND COMPOSITIONS FOR ENHANCING COLLAGEN AND PROTEOGLYCAN SYNTHESIS IN THE SKIN

BACKGROUND OF THE INVENTION

The present invention generally relates to methods and compositions for enhancing collagen and proteoglycan synthesis in the skin.

Over the years attempts have been made to reverse the age-related thinning of the dermis associated with a loss of collagen and changes in quality and quantity of proteoglycans in skin. This has led to the application of creams containing this protein, hydrolyzates of collagen, and a large number of nutrients, hormones, antioxidants, minerals, etc. with little documented success. Unfortunately, large proteins such as collagen cannot traverse the dermal barrier, and smaller molecules do it with difficulty if with any success at all. Alternatively collagen has been injected intradermally with also very limited temporary benefit. Such modality of application is only local and the injected material, being foreign to the body, elicits a tissue reaction and is readily degraded, requiring continual application. In addition such a form of administration does not generate an adequate continuum with the recipient's own collagen and unsightly and undesirable scar-like responses are often evident. Ideally one would want to stimulate the dermal cells to synthesize such collagen in significant amounts to compensate for the age-related loss, and to do so in a uniform fashion.

The thinning, transparency, friability and observable dehydration of skin are characteristics of the aging process, and can be attributed, for the most part, to a loss of collagen and other components of the extracellular matrix such as proteoglycans.

Lipoic acid (thioctic acid) is a naturally occurring 8-carbon dithiol compound wildly distributed in nature (M. Podda et al., "Low Molecular Weight Antioxidants and Their Role in Skin Ageing," *Clin. Exp. Dermatol.* 26: 578-582 (2001); L. Packer, "Oxidants, Antioxidant Nutrients and the Athlete," *J. Sports Sci.* 15: 353-363 (1997)). Although it was initially classified as a vitamin, it was later found to be synthesized by animals and humans. It functions as a cofactor in the multi-enzyme complexes that catalyzes the oxidative decarboxylation of α-keto acids. When supplied endogenously to cells, tissues and whole animals it exerts powerful antioxidant effects. These effects seem to be due to direct radical scavenging and metal chelating by both α-lipoic acid and its reduced form dihydrolipoic acid (G. P. Biewenga et al., "The Pharmacology of the Antioxidant Lipoic Acid," *Gen. Pharmacol.* 29: 315-331 (1997)).

Lipoic acid has been used to treat diabetic polyneuropathy for many years and promoted as an "anti-aging" compound in light of its anti-oxidant activity (L. Packer, "Antioxidant Properties of Lipoic Acid and Its Therapeutic Effects in Prevention of Diabetes Complications and Cataracts," *Ann. N.Y. Acad. Sci.* 738: 257-264 (1994); J. Teichert et al., "Investigations on the Pharmacokinetics of Alpha-Lipoic Acid in Healthy Volunteers," Int. J. Clin. Pharmacol. Ther.: 36: 625-268 (1998); G. P. Biewenga et al. (1997), supra; Packer (1997), supra). Lipoic acid has also been used in an attempt to prevent inflammatory skin damage (U.S. Pat. No. 5,709,868 to Perricone, incorporated herein by this reference.) Old rats whose diet was supplemented with lipoic acid, showed reduced levels of malondialdehyde, an indicator of lipid peroxidation (T. M. Hagen et al., "(R)-Alpha-Lipoic Acid-Supplemented Old Rats Have Improved Mitochondrial Function, Decreased Oxidative Damage, and Increased Metabolic Rate," *FASEB J.* 13: 411-418 (1999)). Studying rat hepatocytes, it was found that a 2-week dietary supplementation of lipoic acid to older rats prior to cell isolation almost completely reversed age-associated effects on ascorbic acid metabolism (J. Lykkesfeldt et al., "Age-Associated Decline in Ascorbic Acid Concentration, Recycling, and Biosynthesis in Rat Hepatocytes—Reversal with (R)-Alpha-Lipoic Acid Supplementation," *FASEB J.* 12: 1183-1189 (1998)). It has also been found to protect against exercise-induced oxidative stress (S. Khanna et al., "Cytokine-Induced Glucose Uptake in Skeletal Muscle: Redox Regulation and the Role Of Alpha-Lipoic Acid," *Am. J. Physiol.* 276: R1327-R1333 (1999)). It is well known that oxidative stress inducing agents and conditions can cause damage to proteins, lipids, carbohydrates and nucleic acids [Davies, 1999]. Surviving an oxidizing environment is actually one of the greatest challenges faced by living organisms.

To diminish oxidative injury, topically applied antioxidants must reach susceptible cells. It has been shown that α-lipoic acid can effectively penetrate across the skin barrier and that in the process it was reduced to a more active form dihydrolipoic acid (M. Podda et al., "Kinetic Study of Cutaneous and Subcutaneous Distribution Following Topical Application of [7,8-$^{14}$C]rac-α-Lipoic Acid onto Hairless Mice," *Biochem. Pharmacol.* 52: 627-633 (1996)). However, there is still a need for a composition that can incorporate lipoic acid or other antioxidants and be suitable for use on human skin while providing effective penetration of the skin by the lipoic acid or other antioxidants.

Therefore, there is a need for an improved composition that is capable of stimulating the dermal cells to synthesize collagen in order to compensate for the age-related loss of collagen. Preferably, such a composition can be used along with other cosmetics and skin treatments, and can be used in a wide variety of patients and skin types.

SUMMARY OF THE INVENTION

One embodiment of the invention is a composition for topical application to the skin to enhance collagen synthesis comprising:

(1) an antioxidant compound selected from the group consisting of lipoic acid, dihydrolipoic acid, lipoic acid esters, dihydrolipoic acid esters, lipoic acid amides, dihydrolipoic acid amides, salts of lipoic acid, salts of dihydrolipoic acid, bioflavonoids, constituents of ginkgo, isoflavones, and mixtures thereof, in a quantity sufficient to enhance collagen synthesis in the skin;

(2) an organic penetrant in which the antioxidant compound is soluble in a sufficient quantity that a concentration of the antioxidant compound sufficient to enhance collagen synthesis can be applied topically and penetrate the skin;

(3) a mixture of essential amino acids comprising:
  (a) from about 5% to about 20% of isoleucine;
  (b) from about 5% to about 20% of leucine;
  (c) from about 10% to about 25% of lysine;
  (d) from about 2% to about 35% of methionine;
  (e) from about 5% to about 20% of phenylalanine;
  (f) from about 5% to about 25% of threonine;
  (g) from about 5% to about 20% of tryptophan;
  (h) from about 10% to about 25% of valine;
  (i) from about 5% to about 20% of histidine; and
  (j) from about 5% to about 20% of arginine; and (4) a topical pharmaceutically acceptable carrier.

Typically, the antioxidant compound is selected from the group consisting of lipoic acid, dihydrolipoic acid, lipoic acid esters, dihydrolipoic acid esters, lipoic acid amides, dihydrolipoic acid amides, salts of lipoic acid, and salts of dihydrolipoic acid. Preferably, the antioxidant compound is lipoic acid or dihydrolipoic acid.

Alternatively, the antioxidant is a bioflavonoid. Typically, the bioflavonoid is selected from the group consisting of quercetin, quercitrin, kaempferol, kaempferol 3-rutinoside, 3'-methoxy kaempferol 3-rutinoside, 5,8,4'-trihydroxyl-6,7-dimethoxyflavone, catechin, epicachetin, epicachetin gallate, epigallocachetin gallate, hesperidin, naringin, rutin, vixetin, proanthocyanidin, apigenin, myricetin, tricetin, quercetin, naringin, kaempferol, luteolin, biflavonyl, silybin, silydianin, and silychristin, and derivatives and glycosides of these compounds. Preferably, the bioflavonoid is proanthocyanidin.

In another alternative, the antioxidant is a constituent of ginkgo. Typically, the constituent of ginkgo is selected from the group consisting of ginkgolide A, ginkgolide B, ginkgolide C, and bilobalide.

In yet another alternative, the antioxidant is an isoflavone. Typically, the isoflavone is selected from the group consisting of genistein, genistin, 6"-0-malonylgenistin, 6"-0-acetylgenistin, daidzein, daidzin, 6"-0-malonyidaidzin, 6"-0-acetylgenistin, glycitein, glycitin, 6"-0-malonylglycitin, and 6-0-acetylglycitin.

In still another alternative, the antioxidant can be a mixture of: (1) a compound selected from the group consisting of lipoic acid, dihydrolipoic acid, lipoic acid esters, dihydrolipoic acid esters, lipoic acid amides, dihydrolipoic acid amides, salts of lipoic acid, and salts of dihydrolipoic acid; and (2) a bioflavonoid, a constituent of ginkgo, or an isoflavone.

Typically, the organic penetrant is selected from the group consisting of lower alkyl diols, $C_{10}$-$C_{20}$ fatty acids and esters thereof, and $C_4$-$C_{20}$ optionally substituted aliphatic alcohols. Preferably, the organic penetrant is a $C_4$-$C_{20}$ optionally substituted aliphatic alcohol. More preferably, the $C_4$-$C_{20}$ optionally substituted aliphatic alcohol is substituted with an aromatic substituent. Still more preferably, the $C_4$-$C_{20}$ aliphatic alcohol substituted with an aromatic substituent is selected from the group consisting of benzyl alcohol and phenethyl alcohol. Most preferably, the organic penetrant is benzyl alcohol.

When the antioxidant is lipoic acid, typically it is present in a concentration of from about 0.3% (w/w) to about 2.0% (w/w). Preferably, it is present in a concentration of from about 0.5% (w/w) to about 1.5% (w/w). More preferably, it is present in a concentration of about 1.0% (w/w).

When the organic penetrant is benzyl alcohol, typically it is present in a concentration of from about 1.0% (w/w) to about 15.0% (w/w). Preferably, it is present in a concentration of from about 1.5% (w/w) to about 2.5% (w/w). More preferably, it is present in a concentration of about 2.0% (w/w).

In the mixture of essential amino acids, the methionine typically comprises from about 2% to about 5% of the mixture. The mixture of essential amino acids can further comprise cysteine. When the mixture includes cysteine, typically, the cysteine comprises from about 2% to about 75% of the mixture, preferably about 40% of the mixture. Although cysteine is not an essential amino acid for human nutrition, it is an additional source of organic sulfur. When cysteine comprises about 40% of the mixture, a composition according to the present invention typically comprises about 0.3% of essential amino acids (excluding cysteine) and about 0.2% of cysteine.

Preferably, the mixture of essential amino acids comprises:
  (a) about 8.20% of isoleucine;
  (b) about 10.92% of leucine;
  (c) about 14.20% of lysine;
  (d) about 3.28% of methionine;
  (e) about 8.20% of phenylalanine;
  (f) about 12.02% of threonine;
  (g) about 7.65% of tryptophan;
  (h) about 16.39% of valine;
  (i) about 8.20% of histidine; and
  (j) about 10.92% of arginine.

Typically, the mixture of essential amino acids comprises from about 0.005% (w/v) to about 0.5% (w/w) of the composition. Preferably, the mixture of essential amino acids comprises from about 0.1% (w/w) to about 0.4% (w/w) of the composition. More preferably, the mixture of essential amino acids comprises about 0.3% (w/w) of the composition.

Typically, the composition further comprises a long-chain fatty acid ester of tocopherol. Preferably, the long-chain fatty acid ester of tocopherol is selected from the group consisting of tocopheryl palmitate, tocopheryl myristate, and tocopheryl stearate. More preferably, the long-chain fatty acid ester of tocopherol is tocopheryl palmitate.

Typically, the composition also further comprises a long-chain fatty acid ester of ascorbic acid. Preferably, the long-chain fatty acid ester of ascorbic acid is selected from the group consisting of ascorbyl palmitate, ascorbyl myristate, and ascorbyl stearate. More preferably, the long-chain fatty acid ester of ascorbic acid is ascorbyl palmitate.

Typically, the topical pharmaceutically acceptable carrier comprises:
  (a) water;
  (b) propylene glycol;
  (c) carbopol;
  (d) an octyl ester of a long-chain fatty acid selected from the group consisting of octyl palmitate, octyl stearate, and octyl myristate.
  (e) silicone fluid;
  (f) cetearyl alcohol;
  (g) triethanolamine; and
  (h) at least one non-sensitizing preservative.

Typically, the octyl ester of the long-chain fatty acid is octyl palmitate. Typically, the at least one non-sensitizing preservative comprises at least one of methylparaben, ethylparaben, propylparaben, butylparaben, and diazolidinyl urea. Preferably, the at least one non-sensitizing preservative comprises methylparaben, propylparaben, and diazolidinyl urea.

The topical pharmaceutically acceptable carrier can comprise other ingredients, such as: (1) a surface-coated starch polymer; (2) a long-chain fatty acid isopropyl ester selected from the group consisting of isopropyl palmitate, isopropyl myristate, and isopropyl stearate, which is typically isopropyl palmitate; (3) a mixture of glyceryl stearate and PEG-100 stearate; (4) a long-chain fatty acid selected from the group consisting of palmitic acid, stearic acid, and myristic acid, which is typically stearic acid; (5) caprylic/capric triglyceride; (6) cetearyl alcohol; (7) caprylic/capric stearyl triglyceride; and (8) fragrance, which typically comprises natural lavender and chamomile oils.

Typically, the composition enhances the synthesis of at least one sulfur-containing antioxidant in vivo when applied to the skin of a user. Preferably, the at least one sulfur-containing antioxidant whose synthesis is enhanced in vivo is glutathione.

Typically, the composition enhances the synthesis of proteoglycans when applied to the skin of a user.

Typically, the composition provides organic sulfate to act as a precursor of proteoglycans when applied to the skin of a user.

Typically, the composition enhances the thickness of the dermis and epidermis when applied to the skin of a user.

Typically, the composition generates sustainable hydration of the epidermis when applied to the skin of a user.

Another aspect of the invention is a method of stimulating collagen synthesis in skin in vivo comprising applying a composition of the present invention, as described above, to skin in a quantity effective to stimulate collagen synthesis in the skin.

Similarly, another aspect of the invention is a method of enhancing the synthesis of at least one sulfur-containing antioxidant in vivo comprising applying a composition of the present invention to skin in a quantity effective to enhance the synthesis of at least one sulfur-containing antioxidant in vivo. Typically, the at least one sulfur-containing antioxidant is glutathione.

Yet another aspect of the invention is a method of enhancing the synthesis of a proteoglycan in vivo comprising applying a composition of the present invention to skin in a quantity effective to enhance the synthesis of a proteoglycan in vivo.

Yet another aspect of the invention is a method of providing organic sulfate to act as a precursor of proteoglycans in vivo comprising applying a composition of the present invention to skin in a quantity effective to provide organic sulfate to act as a precursor of proteoglycans.

Still another aspect of the present invention is a method of enhancing the thickness of epidermis and dermis comprising applying a composition of the present invention to skin in a quantity effective to enhance the thickness of epidermis and dermis.

Yet another aspect of the present invention is a method of generating sustainable hydration of epidermis comprising applying a composition of the present invention to skin in a quantity effective to generate sustainable hydration of the epidermis.

BRIEF DESCRIPTION OF THE DRAWINGS

The following invention will become better understood with reference to the specification, appended claims, and accompanying drawings, where:

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The ability to stimulate collagen production by the transdermal delivery of compounds included in the formulation of the present invention makes it possible to reverse some of the age-related changes described above. In addition the presence of an essential sulfur-amino acid in our mixture, a precursor of glycosaminoglycans present in proteoglycans, is likely to enhance the synthesis of these water retaining molecules, by making available inorganic sulfate to the organism as shown during oral supplementation of sulfur containing supplements (F. Cordoba & M. Nimni, "Chondroitin Sulfate and Other Sulfate Containing Chondroprotective Agents May Exhibit Their Effects by Overcoming a Deficiency of Sulfur Amino Acids," *Osteoarthritis & Cartilage* 11: 228-230 (2003)).

Accordingly, one aspect of the invention is a composition for topical application to the skin to enhance collagen synthesis. The composition is applied directly to the skin.

In general, a composition according to the present invention for topical application to the skin to enhance collagen synthesis comprises:

(1) an antioxidant compound selected from the group consisting of lipoic acid, dihydrolipoic acid, lipoic acid esters, dihydrolipoic acid esters, lipoic acid amides, dihydrolipoic acid amides, salts of lipoic acid, salts of dihydrolipoic acid, bioflavonoids, constituents of ginkgo, isoflavones, and mixtures thereof, in a quantity sufficient to enhance collagen synthesis in the skin;

(2) an organic penetrant in which the antioxidant compound is soluble in a sufficient quantity that a concentration of the antioxidant compound sufficient to enhance collagen synthesis can be applied topically and penetrate the skin;

(3) a mixture of essential amino acids comprising:
(a) from about 5% to about 20% of isoleucine;
(b) from about 5% to about 20% of leucine;
(c) from about 10% to about 25% of lysine;
(d) from about 2% to about 35% of methionine;
(e) from about 5% to about 20% of phenylalanine;
(f) from about 5% to about 25% of threonine;

(g) from about 5% to about 20% of tryptophan;
(h) from about 10% to about 25% of valine;
(i) from about 5% to about 20% of histidine; and
(j) from about 5% to about 20% of arginine; and
(4) a topical pharmaceutically acceptable carrier.

In one embodiment, the antioxidant is selected from the group consisting of lipoic acid, dihydrolipoic acid, lipoic acid esters, dihydrolipoic acid esters, lipoic acid amides, dihydrolipoic acid amides, salts of lipoic acid, and salts of dihydrolipoic acid. Lipoic acid, also known as α-lipoic acid, thioctic acid, 1,2-dithiolane-3-pentanoic acid, and 1,2-dithiolane-3-valeric acid, has the following structural formula:

The disulfide (S—S) bond of lipoic acid is subject to reduction by chemical or biological reducing agents, leading to dihydrolipoic acid, in which the disulfide bond is replaced with two sulfhydryl (SH) groups. Because the two forms are readily interchangeable in vivo, both lipoic acid and dihydrolipoic acid, as well as their derivatives such as esters, amides, and salts, can be used in compositions according to the present invention.

In another embodiment, the antioxidant is a bioflavonoid. Typically, the bioflavonoid is selected from the group consisting of quercetin, quercitrin, kaempferol, kaempferol 3-rutinoside, 3'-methoxy kaempferol 3-rutinoside, 5,8,4'-trihydroxyl-6,7-dimethoxyflavone, catechin, epicachetin, epicachetin gallate, epigallocachetin gallate, hesperidin, naringin, rutin, vixetin, proanthocyanidin, apigenin, myricetin, tricetin, quercetin, naringin, kaempferol, luteolin, biflavonyl, silybin, silydianin, and silychristin, and derivatives and glycosides of these compounds. Bioflavonoids are described, for example, in U.S. Pat. No. 6,576,271 to Nair et al., incorporated herein by this reference. Typically, the bioflavonoid is proanthocyanidin.

In yet another embodiment, the antioxidant is a constituent of ginkgo. Typically, the constituent of ginkgo is selected from the group consisting of ginkgolide A, ginkgolide B, ginkgolide C, and bilobalide.

In yet another embodiment, the antioxidant is an isoflavone. Typically, the isoflavone is selected from the group consisting of genistein, genistin, 6"-0-malonylgenistin, 6"-0-acetylgenistin, daidzein, daidzin, 6"-0-malonyldaidzin, 6"-0-acetylgenistin, glycitein, glycitin, 6"-0-malonylglycitin, and 6-0-acetylglycitin. Preferably, the isoflavone is genistein or daidzein. Isoflavones can be isolated from soy or other phytochemical sources. One isolation process is disclosed in U.S. Pat. No. 6,565,912 to Gugger et al., incorporated herein by this reference.

In still another alternative, the antioxidant can be a mixture of: (1) a compound selected from the group consisting of lipoic acid, dihydrolipoic acid, lipoic acid esters, dihydrolipoic acid esters, lipoic acid amides, dihydrolipoic acid amides, salts of lipoic acid, and salts of dihydrolipoic acid; and (2) a bioflavonoid, a constituent of ginkgo, or an isoflavone. Various mixtures of lipoic acid and other biological antioxidants can be used.

Mixtures of antioxidants can alternatively be used. For example, the antioxidant can be a mixture of: (1) a compound selected from the group consisting of lipoic acid, dihydrolipoic acid, lipoic acid esters, dihydrolipoic acid esters, lipoic acid amides, dihydrolipoic acid amides, salts of lipoic acid, and salts of dihydrolipoic acid; and (2) a bioflavonoid, a constituent of ginkgo, or an isoflavone. The mixture of antioxidants can be chosen by one of ordinary skill in the art to achieve a particularly desirable result, taking into account skin type, age of the expected user, conditions affecting the elasticity or firmness of the skin, or other factors affecting skin condition.

Typically, the organic penetrant is selected from the group consisting of lower alkyl diols, $C_{10}$-$C_{20}$ fatty acids and esters thereof, and $C_4$-$C_{20}$ optionally substituted aliphatic alcohols. Preferably, the organic penetrant is a $C_4$-$C_{20}$ optionally substituted aliphatic alcohol. More preferably, the $C_4$-$C_{20}$ optionally substituted aliphatic alcohol is substituted with an aromatic substituent. Still more preferably, the $C_4$-$C_{20}$ optionally substituted aliphatic alcohol is benzyl alcohol or phenethyl alcohol. Most preferably, the $C_4$-$C_{20}$ optionally substituted aliphatic alcohol is benzyl alcohol. However, other alcohols substituted with an aromatic substituent can alternatively be used.

When the antioxidant is lipoic acid, it is typically present in the composition in a concentration of from about 0.3% (w/w) to about 2.0% (w/w). Preferably, the lipoic acid is present in the composition in a concentration of from about 0.5% (w/w) to about 1.5% (w/w). More preferably, the lipoic acid is present in a concentration of about 1.0% (w/w). Unless stated otherwise, all other percentages of ingredients specified herein are (w/w).

When the antioxidant is proanthocyanidin, it is typically present in the composition in a concentration of from about 0.3% (w/w) to about 2.0% (w/w). Preferably, the proanthocyanidin is present in the composition in a concentration of from about 0.5% (w/w) to about 1.5% (w/w). More preferably, the proanthocyanidin is present in a concentration of about 1.0% (w/w).

When the organic penetrant is benzyl alcohol, it is typically present in the composition in a concentration of from about 1.0% (w/w) to about 15.0% (w/w). Preferably, the benzyl alcohol is present in the composition in a concentration of from about 1.5% (w/w) to about 2.5% (w/w). More preferably, the benzyl alcohol is present in the composition at a concentration of about 2.0% (w/w).

Typically, the methionine comprises from about 2% to about 5% by weight of the mixture of essential amino acids. However, as indicated above, it can be incorporated in the mixture in a greater proportion, i.e., up to about 35% by weight of the mixture of essential amino acids.

In another alternative, the mixture of essential amino acids can further comprise cysteine. Although cysteine is nutritionally not an essential human acid in the human diet, it can be included as a source of organic sulfur. When the mixture of essential amino acids further comprises cysteine, typically, the cysteine comprises from about 2% to about 75% of all amino acids in the mixture by weight; more typically, the cysteine comprises from about 25% to about 75% of all amino acids in the mixture by weight. Preferably, the cysteine comprises about 40% of all amino acids in the mixture by weight. As used herein, recitation of cysteine and other amino acids refers to the naturally-occurring L optical isomer of these amino acids, as that is the isomer that is incorporated into proteins.

Typically, the mixture of essential amino acids (not including cysteine) comprises:
(1) about 8.20% of isoleucine;
(2) about 10.92% of leucine;
(3) about 14.20% of lysine;
(4) about 3.28% of methionine;

(5) about 8.20% of phenylalanine;
(6) about 12.02% of threonine;
(7) about 7.65% of tryptophan;
(8) about 16.39% of valine;
(9) about 8.20% of histidine; and
(10) about 10.92% of arginine.

Typically, the mixture of essential amino acids (including methionine, but not including cysteine) comprises from about 0.005% (w/w) to about 0.5% (w/w) of the composition. Preferably, the mixture of essential amino acids (including methionine, but not including cysteine) comprises from about 0.1% (w/w) to about 0.4% (w/w) of the composition. More preferably, the mixture of essential amino acids (including methionine, but not including cysteine) comprises about 0.3% (w/w) of the composition. As indicated above, this does not include cysteine, which is preferred. Cysteine typically comprises from about 0.01% (w/w) to about 0.4% (w/w) of the composition. Preferably, cysteine comprises about 0.2% (w/w) of the composition.

Other ingredients can also be used. For example, the composition can further comprise a long-chain fatty acid ester of tocopherol. Typically, the long-chain fatty acid ester of tocopherol is selected from the group consisting of tocopheryl palmitate, tocopheryl myristate, and tocopheryl stearate. Preferably, the long-chain fatty acid ester of tocopherol is tocopheryl palmitate. Typically, the long-chain fatty acid ester of tocopherol is present in the composition at a concentration of from about 0.01% (w/w) to about 3.0% (w/w). Preferably, the long-chain fatty acid ester of tocopherol, such as tocopheryl palmitate, is present in the composition at a concentration of about 0.3% (w/w).

Similarly, the composition can further comprise a long-chain fatty acid ester of ascorbic acid. Typically, the long-chain fatty acid ester of ascorbic acid is selected from the group consisting of ascorbyl palmitate, ascorbyl myristate, and ascorbyl stearate. Preferably, the long-chain fatty acid ester of ascorbic acid is ascorbyl palmitate. Typically, the long-chain fatty acid ester of ascorbic acid is present in the composition at a concentration of from about 0.1% (w/w) to about 0.6% (w/w). Preferably, the long-chain fatty acid ester of ascorbic acid, such as ascorbyl palmitate, is present in the composition at a concentration of about 0.3% (w/w).

Suitable topical pharmaceutically acceptable carriers are disclosed in U.S. Pat. No. 5,935,994, incorporated herein by this reference. The carrier is typically in the form of a cream base that is compatible with all of the ingredients as far as stability is concerned.

Typically, the topical pharmaceutically acceptable carrier comprises:
(1) water;
(2) propylene glycol;
(3) carbopol;
(4) an octyl ester of a long-chain fatty acid selected from the group consisting of octyl palmitate, octyl stearate, and octyl myristate.
(5) silicone fluid;
(6) cetearyl alcohol;
(7) triethanolamine; and
(8) at least one non-sensitizing preservative.

A suitable silicone fluid is a silicone fluid with a viscosity of 200 cs.

A suitable preparation of carbopol is Carbopol 940. Other carboxypolymethylene polymers are known in the art, such as Carbomer polymers, and can be used.

Triethanolamine is a buffer and can be replaced by other buffers that can buffer the topical pharmaceutically acceptable carrier to a physiological pH.

Typically, the octyl ester of a long-chain fatty acid is selected from the group consisting of octyl palmitate, octyl stearate, and octyl myristate is octyl palmitate.

The topical pharmaceutically acceptable carrier can further comprise other, optional, ingredients.

For example, the topical pharmaceutically acceptable carrier can further comprise a surface-coated starch polymer. A suitable surface-coated starch polymer is Dryflo PC, marketed by National Starch.

The topical pharmaceutically acceptable carrier can also further comprise a long-chain fatty acid isopropyl ester selected from the group consisting of isopropyl palmitate, isopropyl myristate, and isopropyl stearate. Typically, the long-chain fatty acid isopropyl ester is isopropyl palmitate.

The topical pharmaceutically acceptable carrier can also further comprise a mixture of glyceryl stearate and PEG-100 stearate. A suitable mixture of glyceryl stearate and PEG-100 stearate is Arlacel 165.

The topical pharmaceutically acceptable carrier can also further comprise a long-chain fatty acid selected from the group consisting of palmitic acid, stearic acid, and myristic acid. Typically, the long-chain fatty acid is stearic acid.

The topical pharmaceutically acceptable carrier can also further comprise caprylic/capric triglyceride. A suitable caprylic/capric triglyceride is Miglyol 812.

The topical pharmaceutically acceptable carrier can also further comprise cetearyl alcohol.

The topical pharmaceutically acceptable carrier can also further comprise caprylic/capric stearyl triglyceride. A suitable caprylic/capric stearyl triglyceride is Softisan 378.

The topical pharmaceutically acceptable carrier can also further comprise fragrance. Typically, the fragrance comprises natural lavender and chamomile oils. However, other fragrances are well known in the art of preparing products suitable for application to the skin, and can be used as alternatives.

Typically, the non-sensitizing preservative of the topical pharmaceutically acceptable carrier comprises at least one of methylparaben, ethylparaben, propylparaben, butylparaben, and diazolidinyl urea. Preferably, the non-sensitizing preservative comprises methylparaben, propylparaben, and diazolidinyl urea. A suitable preparation of diazolidinyl urea is Germall 2.

Other ingredients are well known in the art of preparing cosmetics and other products suitable for application for the skin, and can be used in the topical pharmaceutically acceptable carrier. For example, other lipid-soluble components can be used in addition to or in place of the caprylic/capric triglycerides. Such components can include but are not limited to: steareth-2; steareth-21; polyglyceryl-3 beeswax; a branched-chain carboxylic acid ester of a branched-chain alcohol selected from the group consisting of isononyl isononanoate, isodecyl isononanoate, isooctyl isononanoate, isononyl isooctanoate, isodecyl isooctanoate, isooctyl isooctanoate, isononyl isodecanoate, isooctyl isodecanoate, and isodecyl isodecanoate; acrylates/$C_{10}$-$C_{30}$ alkyl acrylates cross-polymers; methylgluceth-20; a glyceryl ester of a long-chain fatty acid selected from the group consisting of glyceryl monostearate, glyceryl monopalmitate, and glyceryl monoarachidate; hydrogenated vegetable oil; squalane; $C_{12}$-$C_{15}$ alkylbenzoates; di-$C_{12}$-$C_{15}$ alkylfumarate; cholesterol; lanolin alcohol; octyldodecanol; isostearic acid; a branched-chain neopentanoate selected from the group consisting of octyldodecyl neopentanoate, heptyldodecyl neopentanoate, nonyldodecyl neopentanoate, octylundecyl neopentanoate, heptylundecyl neopentanoate, nonylundecyl neopentanoate, octyltridecyl neopentanoate, heptyltridecyl neopentanoate, and nonyltridecyl neopentanoate; an arachidyl ester of a short-chain carboxylic acid selected from the group consisting of arachidyl propionate, arachidyl acetate, arachidyl butyrate, and arachidyl isobutyrate; jojoba oil; a myristyl ester of a long-chain fatty acid selected from the group consisting of myristyl myristate, myristyl laurate, and myristyl palmitate; bisabolol; hydrogenated jojoba oil; jojoba esters; methylgluceth-20 sesquistearate; PPG-14 butyl ether; PPG-15 stearyl ether; PPG-1-isoceteth-3-acetate; laureth-2-benzoate; diisostearyl dimer dilinoleate; a long-chain cis-monounsaturated fatty acid ester of a medium-chain alcohol; a medium-chain saturated carboxylic acid ester of a long-chain alcohol; hydrogenated soy glycerides; a long-chain fatty acid ester of cetyl alcohol selected from the group consisting of cetyl palmitate, cetyl stearate, and cetyl myristate; palm kernel oil; and palm oil.

In addition, the topical pharmaceutically acceptable carrier can further comprise other ingredients that are generally used in the cosmetic art and in the art of over-the-counter skin preparations. These ingredients include, but are not limited to:

(1) plant extracts, such as horsetail extract, horse chestnut extract, rose extract, or lavender extract;

(2) a long-chain fatty acid ester of retinol or a retinol derivative or analogue wherein the acyl moiety of the ester is selected from the group consisting of myristic acid, palmitic acid, and stearic acid; and (3) a sunscreen, which can be at least one compound selected from the group consisting of octyl methoxycinnamate, p-aminobenzoic acid, ethyl p-aminobenzoate, isobutyl p-aminobenzoate, glyceryl p-aminobenzoate, p-dimethylaminobenzoic acid, methyl anthranilate, menthyl anthranilate, phenyl anthranilate, benzyl anthranilate, phenylethyl anthranilate, linalyl anthranilate, terpinyl anthranilate, cyclohexenyl anthranilate, amyl salicylate, phenyl salicylate, benzyl salicylate, menthyl salicylate, glyceryl salicylate, dipropyleneglycol salicylate, methyl cinnamate, benzyl cinnamate, .alpha.-phenyl cinnamonitrile, butyl cinnamoylpyruvate, umbelliferone, methylacetoumbelliferone, esculetin, methylesculetin, daphnetin, esculin, daphnin, diphenylbutadiene, stilbene, dibenzalacetone, benzalacetophenone, sodium 2-naphthol-3,6-disulfonate, sodium 2-naphthol-6,8-disulfonate, dihydroxynaphthoic acid, salts of dihydroxynaphthoic acid, o-hydroxybiphenyldisulfonates, p-hydroxybiphenyldisulfonates, 7-hydroxycoumarin, 7-methylcoumarin, 3-phenylcoumarin, 2-acetyl-3-bromoindazole, phenylbenzoxazole, methylnaphthoxazole, arylbenzothiazoles, quinine bisulfate, quinine sulfate, quinine chloride, quinine oleate, quinine tannate, 8-hydroxyquinoline salts, 2-phenylquinoline, hydroxy-substituted benzophenones, methoxy-substituted benzophenones, uric acid, vilouric acid, tannic acid, tannic acid hexaethylether, hydroquinone, oxybenzone, sulisobenzone, dioxybenzone, benzoresorcinol, 2,2',4,4'-tetrahydroxybenzo-phenone, 2,2'-dihydroxy-4,4'-dimethoxybenzophenone, octabenzone, 4-isopropyldibenzoylmethane, butylmethoxydibenzoylmethane, etocrylene, and 4-isopropyldibenzoylmethane.

Other ingredients can optionally be included in the topical pharmaceutically acceptable carrier.

Compositions according to the present invention can be prepared by standard procedures, such as those typically used for cosmetic preparations and pharmaceutical compositions intended for topical application to the skin. These procedures include mixing techniques, including both manual and mechanical mixing, and including homogenization mixing and sweep mixing. The mixing techniques to be used can be chosen by one of ordinary skill in the art based on variables such as the viscosity of the components to be mixed and the volume of those components, as well as the relative proportion of lipid-soluble and water-soluble ingredients. Typically, the individual active ingredients are added sequentially, and benzyl alcohol or the other organic penetrant is added to the desired final concentration. Water and oil phases are heated separately to 70° C., blended, and cooled with normal mixing.

One preferred formulation of the topical pharmaceutically acceptable carrier is shown in Table 1.

TABLE 1

FORMULATION OF TOPICAL PHARMACEUTICALLY ACCEPTABLE CARRIER

| Ingredient | %(w/w) |
|---|---|
| Propylene glycol | 2.23 |
| Carbopol | 1.12 |
| Surface coated starch polymer | 0.56 |
| Octyl palmitate | 1.12 |
| Isopropyl palmitate | 2.23 |
| Silicone fluid | 2.23 |
| Glyceryl stearate/PEG-100 stearate | 2.23 |
| Cetearyl alcohol | 1.12 |
| Stearic acid | 0.56 |
| Triethanolamine | 0.28 |
| Caprylic/capric triglyceride | 2.23 |
| Caprylic/capric stearyl triglyceride | 0.56 |
| Natural lavender/chamomile oils | 0.22 |
| Methylparaben | 0.22 |
| Propylparaben | 0.06 |
| Diazolidinyl urea | 0.22 |
| Water | q.s. to 100 |

Typically, the composition enhances the synthesis of at least one sulfur-containing antioxidant in vivo when applied to the skin of a user. Typically, the at least one sulfur-containing antioxidant is glutathione, which is a biologically significant reducing agent.

Typically, the composition enhances the synthesis of proteoglycans when applied to the skin of a user.

Typically, the composition also provides organic sulfate to act as a precursor of proteoglycans when applied to the skin of a user.

Typically, the composition also enhances the thickness of the dermis and the epidermis when applied to the skin of a user.

Typically, the composition generates sustainable hydration of the epidermis when applied to the skin of a user. This is evidenced by the thickened and more youthful histological appearance of this structure. The composition therefore can overcome some of the age-related changes in skin.

Compositions according to the present invention can be applied by users as they would apply standard cosmetics or other creams, once or more daily, depending on age, skin condition, and other variables readily apparent to the user.

Accordingly, therefore, another aspect of the invention is a method of stimulating collagen synthesis in skin in vivo comprising applying a composition according to the present invention to skin in a quantity effective to stimulate collagen synthesis in the skin.

Yet another aspect of the invention is a method of enhancing the synthesis of at least one sulfur-containing antioxidant in vivo comprising applying a composition according to the present invention to skin in a quantity effective to enhance the synthesis of at least one sulfur-containing antioxidant in vivo. Typically, the at least one sulfur-containing antioxidant is glutathione.

Still another aspect of the invention is a method of enhancing the synthesis of a proteoglycan in vivo comprising applying a composition according to the present invention to skin in a quantity effective to enhance the synthesis of a proteoglycan in vivo. Proteoglycans are complex macromolecules containing protein and carbohydrate components that form part of the ground substance of the skin and contribute greatly to its firmness and elasticity.

Yet another aspect of the invention is a method of providing organic sulfate to act as a precursor of proteoglycans in vivo comprising applying a composition according to the present invention to skin in a quantity effective to provide organic sulfate to act as a precursor of proteoglycans.

Still another aspect of the invention is a method of enhancing the thickness of epidermis and dermis comprising applying a composition according to the present invention to skin in a quantity effective to enhance the thickness of epidermis and dermis.

Still another aspect of the invention is a method of generating sustainable hydration of epidermis comprising applying a composition of claim 1 to skin in a quantity effective to generate sustainable hydration of the epidermis.

The invention is illustrated by the following Examples. These Examples are included for illustrative purposes only, and are not intended to limit the invention.

EXAMPLES

Example 1

Effect of Lipoic Acid and Proanthocyanidin on Collagen Synthesis in Rat Dermis

Materials and Methods

Dermal Application to Rats

Nine adult rats (female retired breeders) were obtained from Hylan (Hylan Co. CA) with average weight 250 g. To the shaved dorsum a basic cream formulations containing the various additives were applied twice daily for 10 days. Additives included 3% benzyl alcohol, which served as a penetration enhancer, and a mixture of essential amino acids. The amino acid mixture was compounded to match the ratios of these amino acids as they are present in human serum. The lipoic acid concentration was 1.0%. The cream was rubbed in gently until it appeared to vanish from the surface. At the end of this period, rats were sacrificed and skin removed for biochemical and histological analysis.

TGF-β and PDGF Assay

Skin from the area where cream was applied was removed and cleaned of hair and attached fat and placed over a bed of ice. One $cm^2$ of skin was homogenized in PBS buffer. For complete release of TGF-β1, extracts were overnight at 4° C. before centrifuging at 1000×g for 15 minutes. The latent form of TGF-β1 was activated by acidification with 2.5 N acetic acid/10 M urea, and TGF-β1 determined by immunoassay (Quantikine, R&D System, Minneapolis, Minn.). PDGF was also tested in tissue extracts with the aid of an immunoassay kit (Quantikine, R& D System).

Collagen Synthesis Assay

Fresh cut-off skin was washed with PBS for 3 times and minced into 1 $mm^2$ pieces on ice. Approximately 200 mg of minced skin was incubated with 2.0 ml 10% FBS/DMEM medium supplemented with 100 μCi/ml [$^{14}$C]proline. Tissues were incubated at 37° C. in a 5% $CO_2$ environment for 2, 4, and 8 hours. At the end of the incubation periods, NaCl granules were added into the medium to a final concentration of 4.0 M. After incubation overnight at 4° C., they were centrifuged at 20,000 rpm for 30 minutes to precipitate collagen. After washing the pellet with 4 M salt three times, pellets were further dialyzed against deionized water for 48 hours. Samples were freeze-dried, weighed and then hydrolyzed with 2 N HCl. Fifty microliters of a neutralized solution was counted with a Beckman scintillation counter.

Histology

Skin was fixed with 10% buffered formalin and embedded in paraffin. Sections, 0.5 μm thick, were cut and stained with hematoxylin and eosin. Slides were viewed with an Olympus BH-2 microscope under tungsten and Polaroid light.

Cell Proliferation Assay

NIH 3T3 fibroblasts were cultured in DMEM containing 10% fetal bovine serum in 24-well plates at a density of $80 \times 10^3$. After overnight attachment, medium was changed to a conditioning medium with different dosages of lipoic acid (20 ng-20 μg). DNA content was assayed after 48 hours in culture. Briefly, cells were trypsinized with 0.25% trypsin-EDTA and pelleted by centrifugation. To the cell pellet, 1.5 ml of cold 10 mM EDTA (pH 12.3) was added to solubilize cells. After neutralizing with 1.0 M $KH_2PO_4$ (140 μl) and mixing with 0.5 ml of 100 mM NaCl/10 mM Tris (pH 7.0), 10 μl of 66.7 μg/ml Hoechst 33258 (Sigma) was added to give fluorescent readings at emissions of 350 nm and 450 nm. Cell numbers were obtained by comparing the reading to a standard curve of cellular DNA ($1 \times 10^4$ to $1 \times 10^6$ fibroblast). [$^3$H] Thymidine incorporation into DNA was performed as previously described (B. Han et al., "Proanthocyanidin: A Natural Crosslinking Reagent for Stabilizing Collagen Matrices," *J. Biomed. Mater. Res.* 65A: 118-24 (2003)).

Effect of Lipoic Acid on Rate of Collagen Synthesis

Rat skin fibroblasts and NIH 3T3 cells were used to measure collagen synthesis in vitro. Cells at a density of $100 \times 10^3$ in 24-well-plates were grown with 10% FBS/DMEM (Irvine Scientific, CA) supplemented with different doses of lipoic acid (0-16 μg/ml). Cells were incubated at 37° C. in a 5% $CO_2$ environment for 24 hours. Medium was changed into labeling medium for another 24 hours (50 μCi/ml [$^3$H]proline, 25 μg/ml ascorbic acid, 25 μg/ml β-aminoproprionitrile (β-APN)). Collagen synthesis from cultured cells was assayed as previously described (B. Han et al. (2003), supra). Briefly, cells and medium were acidified with glacial acetic acid to a final concentration of 0.5 M and pepsin (Worthington) added to a final concentration of 0.5 mg/ml. Plates were shaken overnight at 4° C., collagen precipitated with 4.0 M NaCl and pellets washed with 20% cold ethanol 3 times. Pellets were dissolved with 0.5 M acetic acid and counted with a scintillation counter (Beckman)

Figure 1:
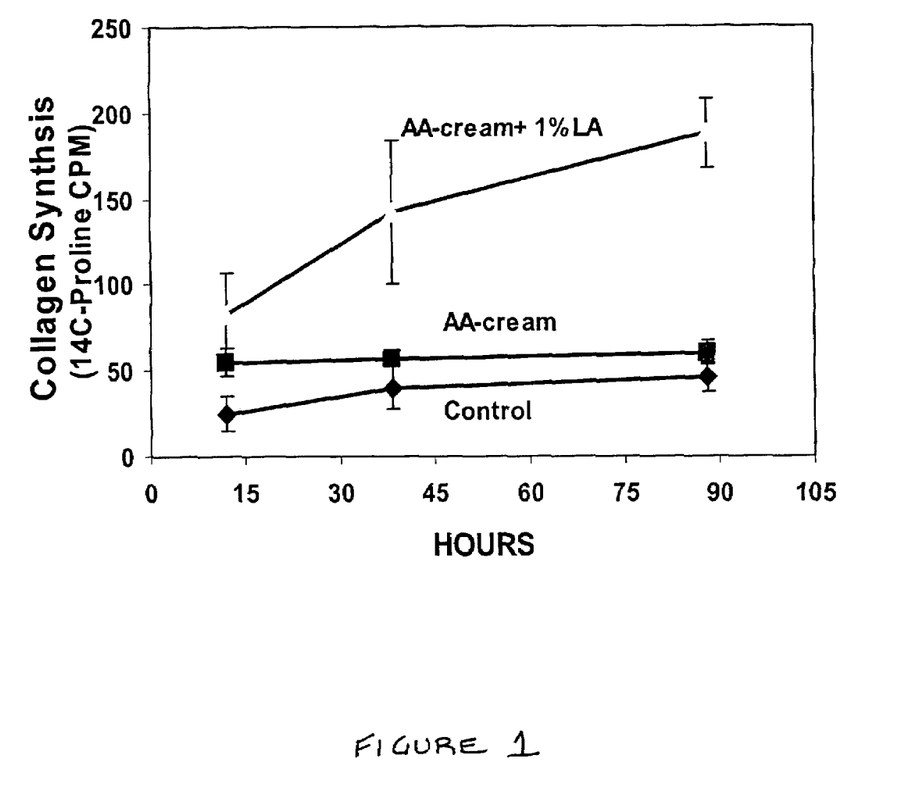
FIG. 1 is a graph showing the effects of a topically applied cream of the present invention containing a mixture of amino acids and antioxidant on collagen synthesis, as well as a composition only containing amino acids, on rat skin using uptake of radioproline as an indicator of collagen synthesis.

Results:

The effects of topically applied cream containing a mixture of amino acids and antioxidant on collagen synthesis in rat skin were investigated using uptake of radioproline into collagen as an index (FIG. 1). In FIG. 1, the rate of radioproline incorporation was measured as a function of time for a control (♦), amino acids alone (■), and for amino acids plus lipoic acid (Δ). The group that was treated with the cream containing amino acid supplements alone showed a slight but not statistically significant increase in rates of collagen synthesis. These increments were consistent and maintained over the period of labeling. The rats, which received the cream containing both amino-acid supplements and an antioxidant, in this example 1% α-lipoic acid, exhibited a significantly enhanced rate of collagen synthesis, which increased during the period of in vitro incubation.

Figure 2:
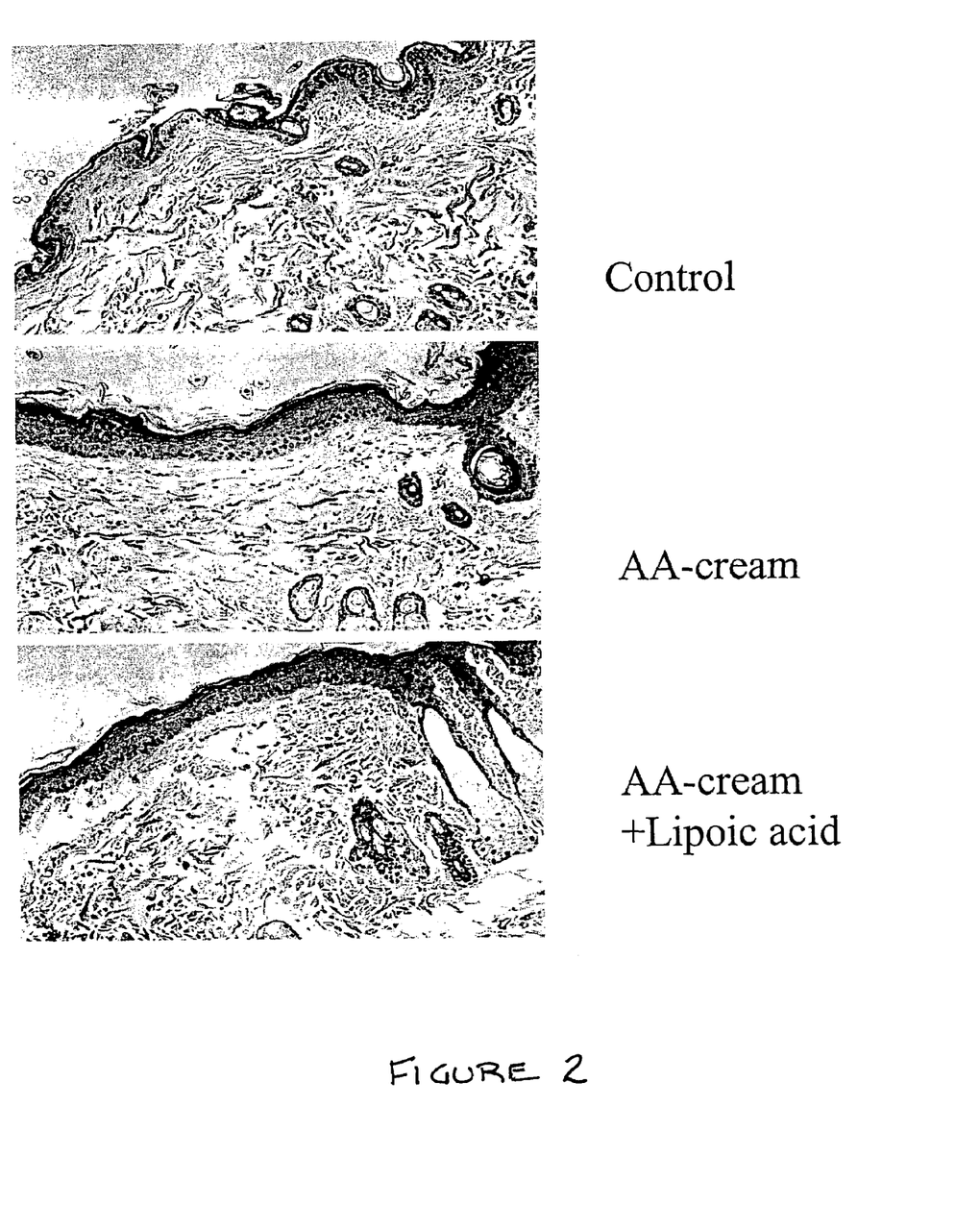
FIG. 2 is a series of photomicrographs showing the effect of the topically applied cream of the present invention on the thickness of epidermis (top panel: control; middle panel: amino acids only; bottom panel: amino acids and lipoic acid)

Histological observation of the explants corroborated the previous observations. The cream containing amino acids enhanced the thickness of the epidermis compared with control (FIG. 2, top panel and 2, middle panel, respectively), while that containing in addition α-lipoic acid further enhanced this structure and the staining characteristics of the cells and extracellular matrix, both in the epidermis and dermis (FIG. 2, bottom panel).

Figure 3:
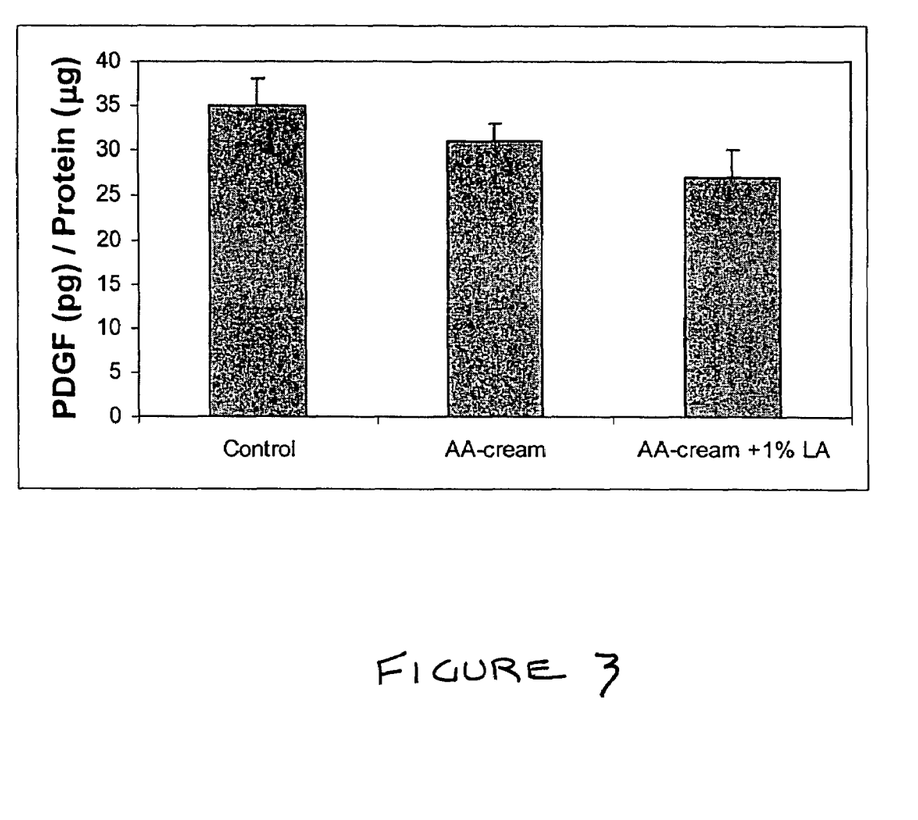
FIG. 3 is a graph showing the levels of PDGF in skin after administration of the topically applied cream of the present invention (leftmost bar: control; middle bar: amino acids only; rightmost bar: amino acids and lipoic acid).
Figure 4:
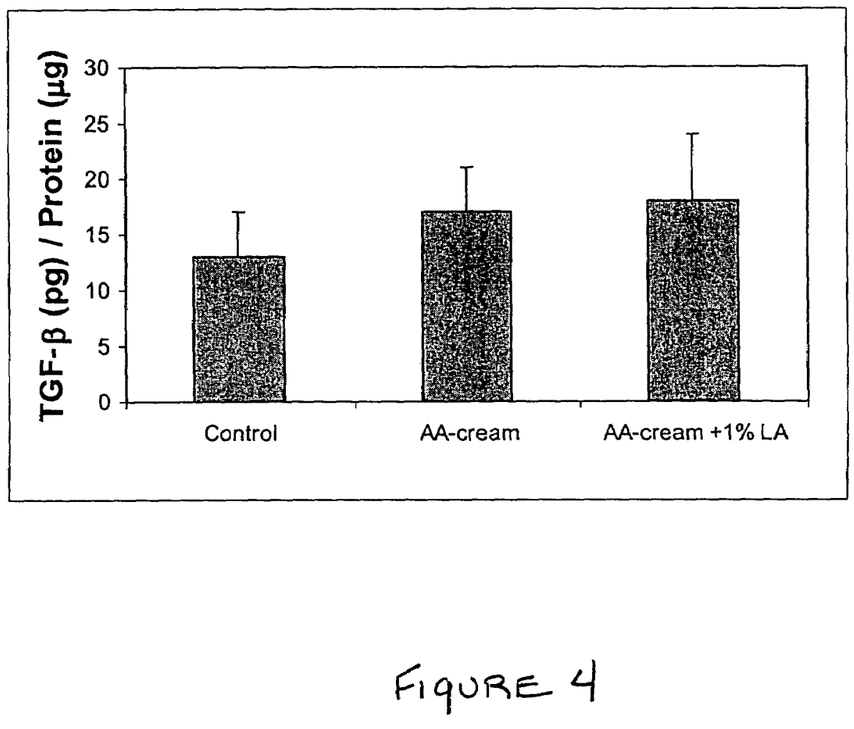
FIG. 4 is a graph showing the levels of TGF-β in skin before and after administration of the topically applied cream of the present invention.

The stimulatory effects on collagen synthesis do not seem to be mediated by changing levels of neither TGF-β1 (FIG. 3) nor PDGF (FIG. 4). In both FIGS. 3 and 4, the leftmost bar represented the level of TGF-β1 (FIG. 3) and PDGF (FIG. 4) in the control. The middle bar, in both figures, represented the levels after treatment with a cream containing only amino acids. The rightmost bar, in both figures, represented the levels after treatment with a cream containing both amino acids and lipoic acid. Levels of these growth factors are not significantly altered by the topical application of these creams. If anything, adding amino acids and lipoic acid to the creams caused a slight but non-statistically significant decline in PDGF activity. In the case of TGF-β1, the slight increments observed cannot be considered significant.

Figure 5:
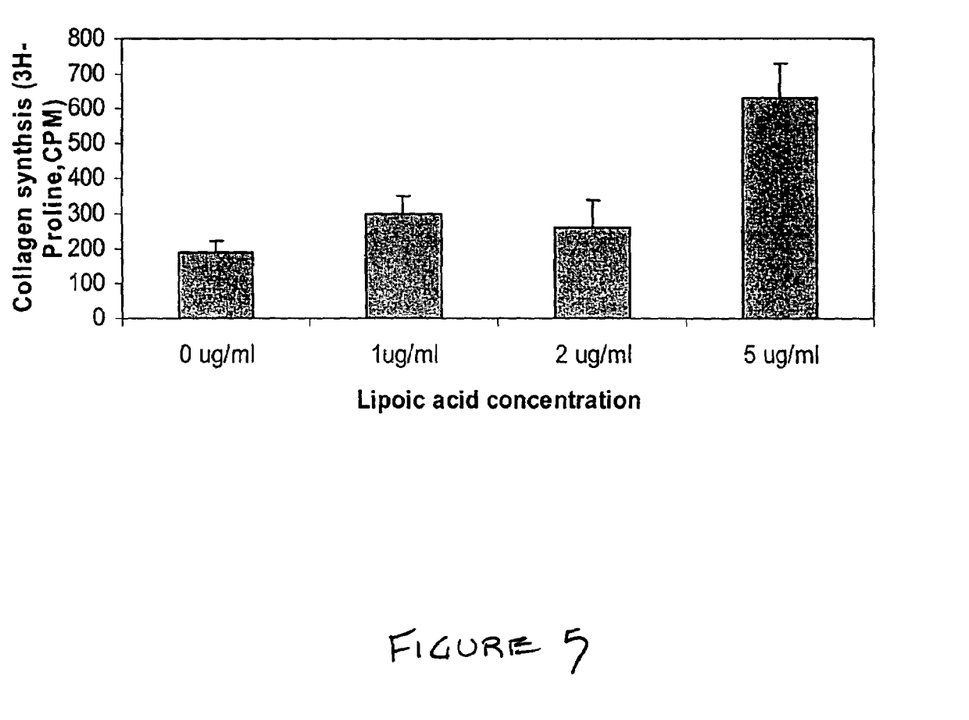
FIG. 5 is a graph showing the effect of a composition according to the present invention containing lipoic acid and amino acids on the synthesis of collagen in vitro using human skin fibroblasts.
Figure 6:
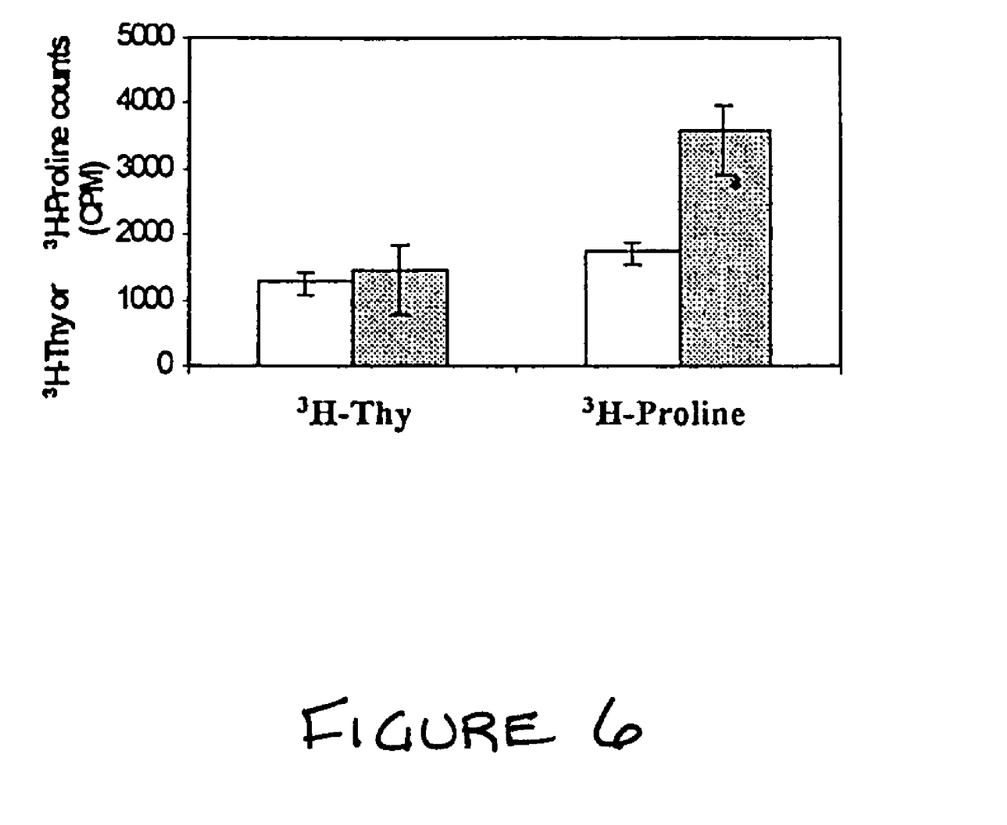
FIG. 6 is a graph showing the effect of proanthocyanidin on the synthesis of collagen in vitro using human skin fibroblasts.

When the effects of lipoic acid and proanthocyanidin were evaluated in vitro, using skin fibroblasts it was consistently observed that collagen synthesis was increased, both with lipoic acid (FIG. 5) and proanthocyanidin (FIG. 6). The results shown in FIGS. 5 and 6 both show increased incorporation of radioproline, which was used as a marker for the synthesis of collagen. In FIG. 5, the results are shown as a function of lipoic acid concentration, from 0 to 5 μg/ml. The results in FIG. 6 also show an increase in cellular proliferation as determined by incorporation of thymidine (group of bars on left side of figure) as well as an increased synthesis of collagen (group of bars on right side of figure). In FIG. 6, the light bars represent the control; the dark bars represent the results of treatment with proanthocyanidin.

These findings show that the administration of antioxidants combined with a balanced mixture of essential amino acids in the form of a cream containing benzyl alcohol, which we have shown to be a good penetration enhancer significantly enhances collagen synthesis in rat skin. This effect does not seem to be mediated by TGF-β1 or PDGF, two growth factors known to stimulate collagen synthesis. The histological appearance of the skin of mature female rat treated with either a balanced mixture of amino acids or lipoic acid or a combination of both, is significantly improved by the presence of such additives. The epidermis is thickened, a characteristic of youthful appearance, and the dermis reflects the greater accumulation of collagen quantified by biochemical measurements.

Since a characteristic feature of aging human skin is a time dependent loss of collagen, which results in a constant thinning of the dermal and epidermal components, the ability of such a mixture to enhance collagen synthesis, should be considered as a practical way of reversing this age-related decline in skin collagen. The combination of antioxidants and a mixture of essential amino acids seem to act synergistically to enhance a thickening of the dermis and epidermis and an increased deposition of collagen in the dermis in rats.

Example 2

Effect of Lipoic Acid on Human Skin In Vivo

The composition used in Example 1 was applied to the skin surface of a number of human volunteers. The effect of the composition on the skin was determined by a modification of the microrelief technique. This technique relies essentially on the application of a polyvinylsiloxane impression material, similar to what dentists use to take impressions in the mouth, to the skin. Upon drying the film is removed and either sputter coated with a conducting metal for visualization using a scanning electron microscope, or more easily with a high power stereomicroscope, and photographed. The technique is simple and reproducible. Each division on the scale equals 0.5 mm.

Figure 7:
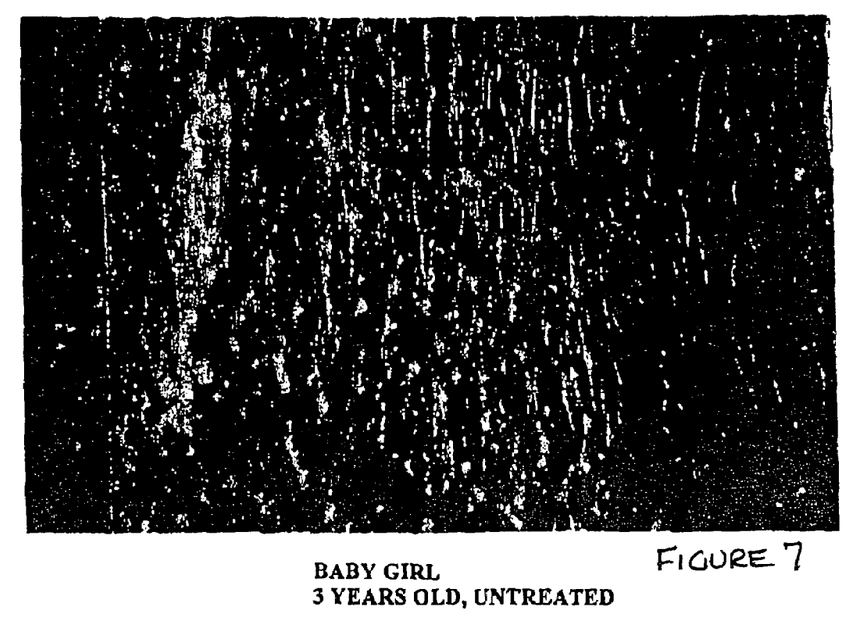
FIG. 7 is a microrelief photomicrograph of skin from a 3-year-old girl.
Figure 8:
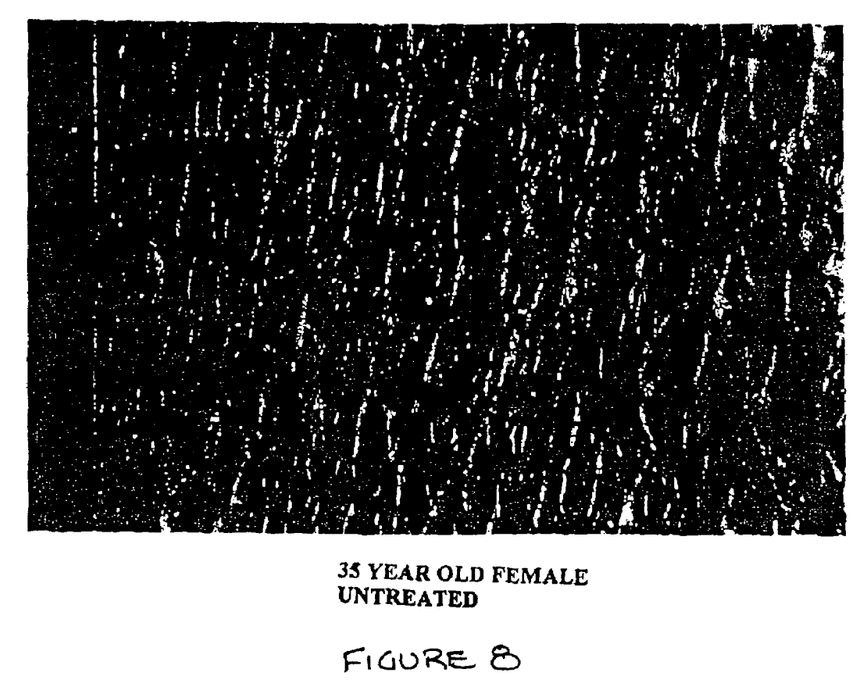
FIG. 8 is a microrelief photomicrograph of skin from the 35-year-old mother of the 3-year-old-girl of FIG. 7, showing age-related changes.

The pattern observed in the skin changes with age, as evidenced by the obvious differences between the pattern seen for a 3-year-old-girl (FIG. 7) and for her 35-year-old mother (FIG. 8). These patterns were obtained without treatment.

Figure 9:
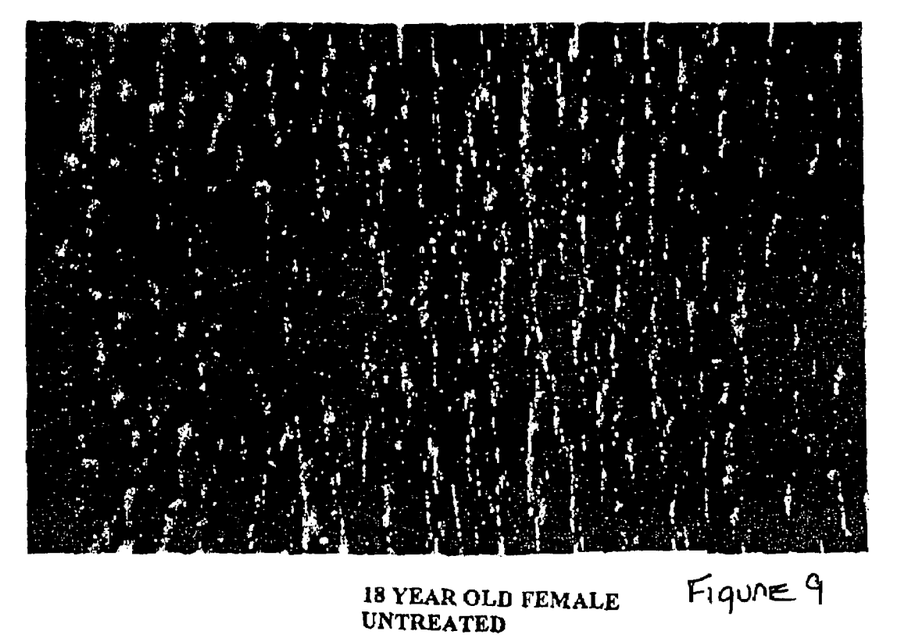
FIG. 9 is a microrelief photomicrograph of skin from a 28-year-old woman before treatment with a composition according to the present invention comprising lipoic acid and essential amino acids.
Figure 10:
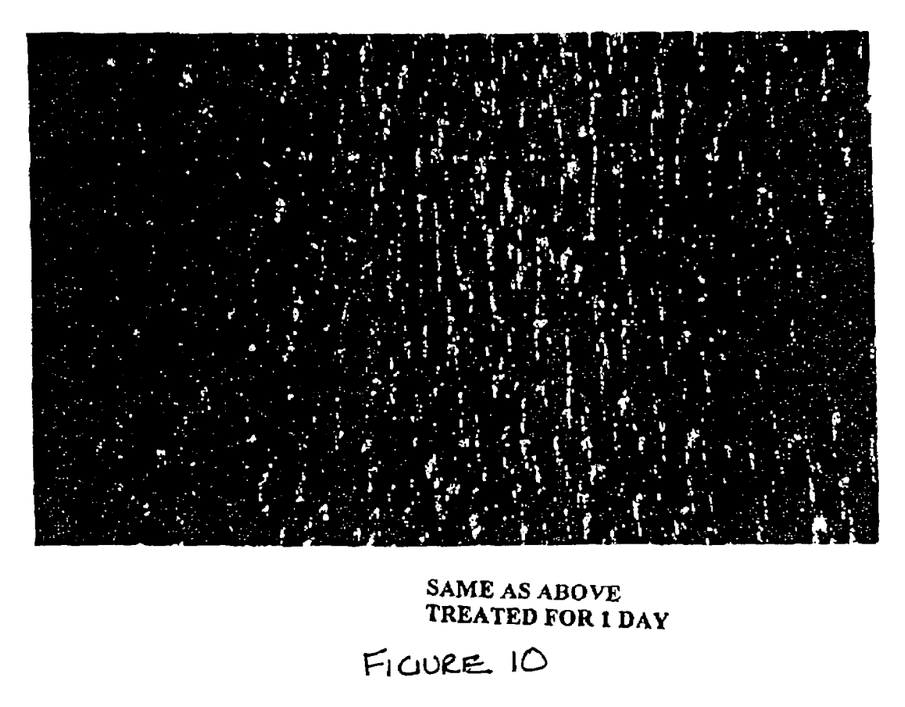
FIG. 10 is a microrelief photograph of skin from the 28-year-old woman of FIG. 9 after 6 days of treatment, showing visually detectable improvement.

FIGS. 9 and 10 show the effect of treatment with the composition used in Example 1 on the skin of a 28-year-old female. FIG. 9 shows the results with the untreated skin; FIG. 10 shows the results after 6 days of treatment. This shows that significant improvement can be noted after as little as 6 days of treatment.

Figure 11:
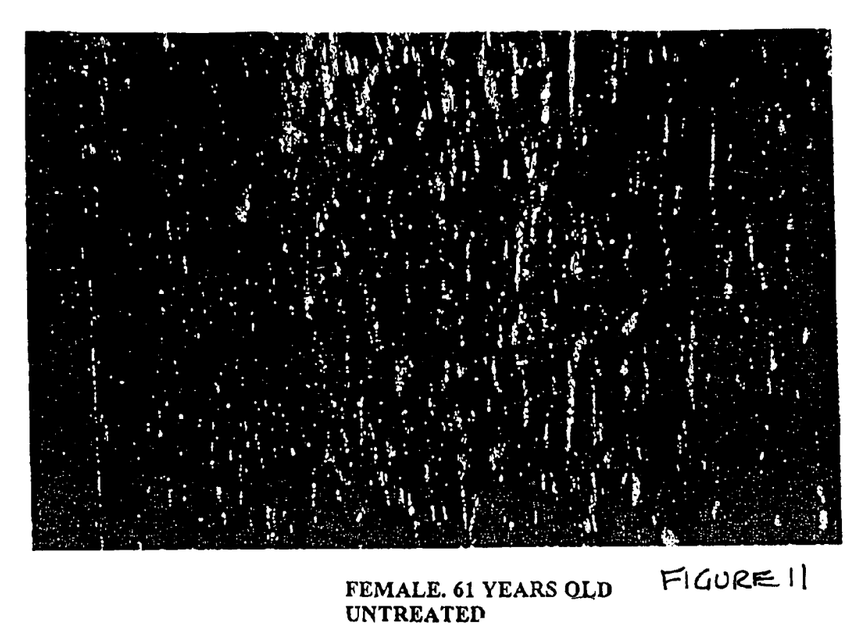
FIG. 11 is a microrelief photomicrograph of skin from a 61-year-old woman before treatment with a composition according to the present invention comprising lipoic acid and essential amino acids.
Figure 12:
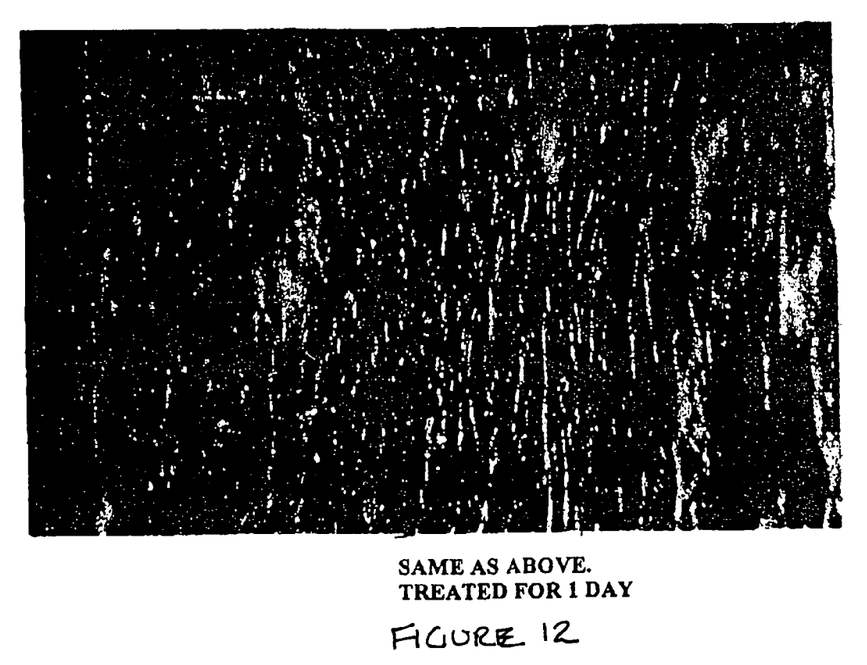
FIG. 12 is a microrelief photomicrograph of skin from the 68-year-old woman of FIG. 9 after 7 days of treatment, showing visually detectable improvement.
Figure 13:
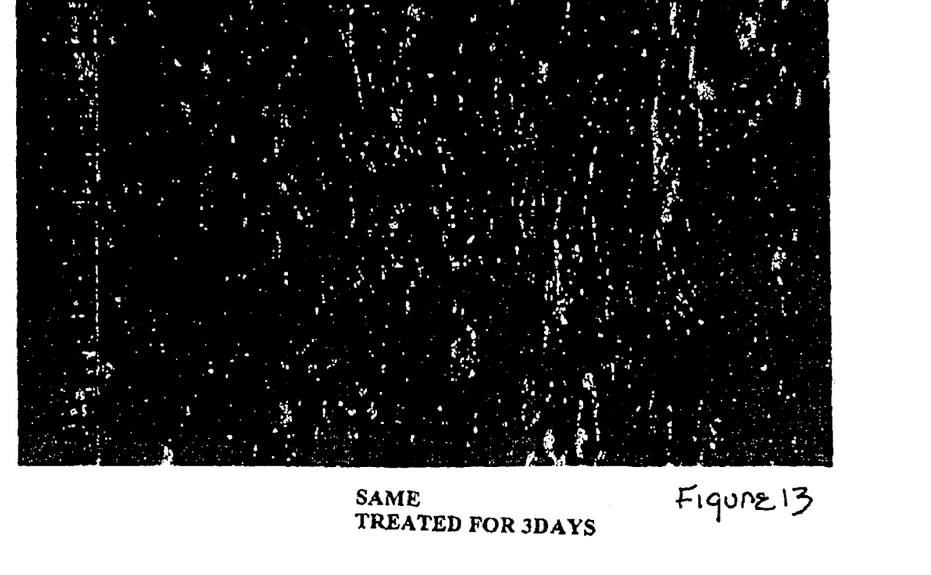
FIG. 13 is a microrelief photomicrograph of skin from the 68-year-old woman of FIG. 9 after 14 days of treatment, showing continued improvement.
Figure 14:
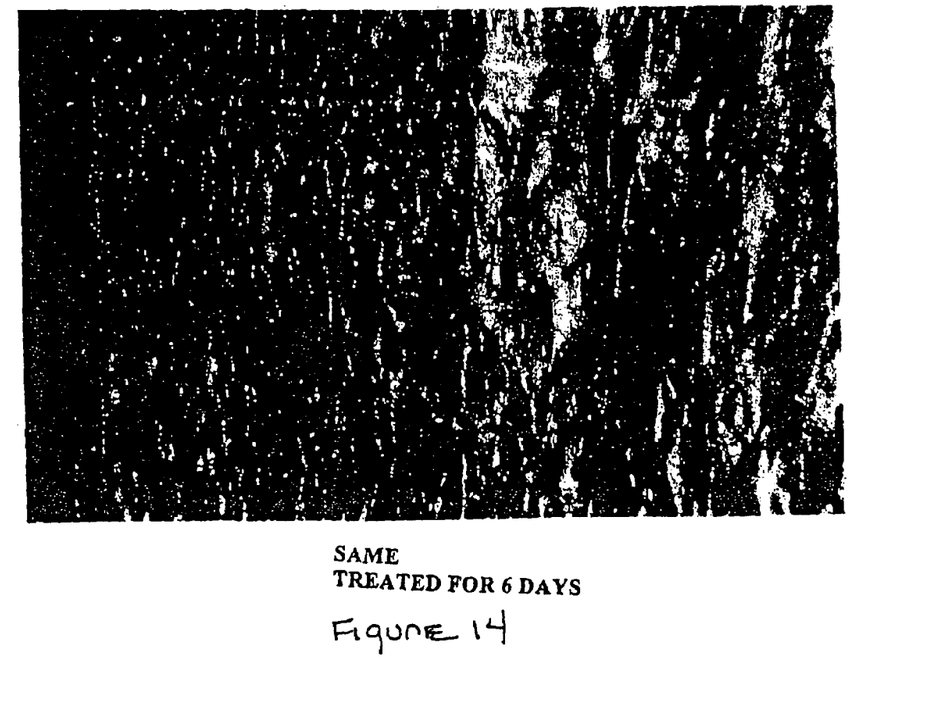
FIG. 14 is a microrelief photomicrograph of skin from the 68-year-old woman of FIG. 9 after 21 days of treatment, showing further improvement.

FIGS. 11-14 show the effect of treatment with the composition used in Example 1 on the skin of a 61-year-old female. FIG. 11 shows the results with the untreated skin; FIG. 12 shows the results after 7 days of treatment; FIG. 13 shows the results after 14 days of treatment; and FIG. 14 shows the results after 21 days of treatment. The significant visual improvement started on day 2 and continued until day 7 when the first microrelief pattern (FIG. 12) was documented, and extended over the 3-week period of study.

ADVANTAGES OF THE INVENTION

Compositions according to the present invention provide an effective way of spurring the synthesis of collagen in the skin of users who apply the compositions. This has the effect of reversing the age-related thinning of the dermis associated with the natural loss of collagen from the skin with age. These compositions have the particular advantage of causing the body to accelerate its production of its own collagen molecules. This is a superior approach to the intradermal injection of collagen, which provides only limited temporary benefit, and causes a tissue reaction from the body to the foreign material. This leads to rapid degradation, requiring continual reapplication. In addition, the administration of extraneous collagen does not generate an adequate continuum with the natural collagen of the recipient and this has negative consequences for the appearance of the skin, including scar-like responses.

Compositions according to the present invention also promote the synthesis of proteoglycans, which form part of the ground substance of the skin. These molecules help retain water and aid in giving the skin its natural firmness and elasticity.

Compositions according to the present invention can be used along with other cosmetics and skin treatments, and can be used in a wide variety of patients and skin types. They are not likely to provoke allergic or inflammatory reactions, and are well tolerated.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

We claim:

1. A composition for topical application to the skin to enhance collagen synthesis consisting of:
   proanthocyanidin as an antioxidant compound, in a quantity of from about 0.3% (w/w) to about 2.0% (w/w);
   (b) an organic penetrant selected from the group consisting of lower alkyl diols, $C_{10}$-$C_{20}$ fatty acids and esters thereof, and $C_4$-$C_{20}$ optionally substituted aliphatic alcohols in a quantity of from of about 1.0% (w/w) to about 15.0% (w/w);
   (c) a mixture of essential amino acids consisting of;
      (i) from about 5% to about 20% of isoleucine;
      (ii) from about 5% to about 20% of leucine;
      (iii) from about 10% to about 25% of lysine;
      (iv) from about 2% to about 35% of methionine;
      (v) from about 5% to about 20% of phenylalanine;
      (vi) from about 5% to about 25% of threonine;
      (vii) from about 5% to about 20% of tryptophan;
      (viii) from about 10% to about 25% of valine;
      (ix) from about 5% to about 20% of histidine; and
      (x) from about 5% to about 20% of arginine, the mixture being present in a quantity sufficient to enhance collagen synthesis in the skin in an individual to which the composition is applied; and
   (d) a topical pharmaceutically acceptable carrier, wherein the pharmaceutically acceptable carrier consists of:
      (i) water;
      (ii) propylene glycol;
      (iii) carbopol;
      (iv) a surface coated starch polymer;
      (v) octyl palmitate;
      vi) isopropyl palmitate;
      (vii) silicone fluid;
      (viii) a mixture of glyceryl stearate and PEG-100 stearate;
      (ix) cetearyl alcohol;
      (x) triethanolainine;
      (xi) caprylic/capric triglyceride;
      (xii) caprylic/capric stearyl triglyceride;
      (xiii) natural lavender oils;
      (xiv) natural chamomile oils;
      (xv) methylparabern;
      (xvi) propylparaben; and
      (xvii) diazolidinyl urea: such that the composition enhances the synthesis of collagen and proteoglycans in skin fibroblasts of an individual to which the composition is applied by the action of the antioxidant compound and the mixture of essential amino acids.

2. The composition of claim 1 wherein the organic penetrant is a $C_4$-$C_{20}$ optionally substituted aliphatic alcohol.

3. The composition of claim 2 wherein the $C_4$-$C_{20}$ optionally substituted aliphatic alcohol is substituted with an aromatic substituent.

4. The composition of claim 3 wherein the $C_4$-$C_{20}$ aliphatic alcohol substituted with an aromatic substituent is selected from the group consisting of benzyl alcohol and phenethyl alcohol.

5. The composition of claim 4 wherein the $C_4$-$C_{20}$ aliphatic alcohol substituted with an aromatic substituent is benzyl alcohol.

* * * * *